United States Patent [19]

Matsuura

[11] Patent Number: 5,288,880

[45] Date of Patent: Feb. 22, 1994

[54] PROCESS FOR THE MANUFACTURE OF MALEIC ANHYDRIDE

[75] Inventor: Ikuya Matsuura, Toyama, Japan

[73] Assignee: Maruzen Petrochemical Co., Ltd., Tokyo, Japan

[21] Appl. No.: 31,600

[22] Filed: Mar. 15, 1993

[30] Foreign Application Priority Data

Mar. 17, 1992 [JP] Japan ................. 4-091822
Nov. 6, 1992 [JP] Japan ................. 4-322373

[51] Int. Cl.$^5$ ............................. C07D 307/60
[52] U.S. Cl. ....................... 549/260; 502/209
[58] Field of Search ............. 549/260; 502/209

[56] References Cited

U.S. PATENT DOCUMENTS 3,862,146 1/1975 Boghosian ................. 260/346.8 A
3,987,063 10/1976 Lemal et al. ............. 260/346.8 A

FOREIGN PATENT DOCUMENTS 1399560 7/1975 United Kingdom .

OTHER PUBLICATIONS

Shokubai, vol. 33, No. 2 pp. 115-118 (1991).

*Primary Examiner*—Bernard Dentz
*Attorney, Agent, or Firm*—Melvin I. Stoltz

[57] ABSTRACT

The present invention provides a process for the manufacture of maleic anhydride by the vapor phase catalytic oxidation of n-butane with molecular oxygen by the use of a specially prepared phosphorus vanadium-oxygen composite catalyst containing specific kind of a divalent metal. The catalyst used in the present invention is prepared from a mixture of vanadyl hydrogen orthophosphate and at least one compound selected from the group consisting of a divalent metal hydrogen orthophosphate (Divalent metal is selected from Mg, Ca, Ba, Mn, Fe, Co, Ni, Cu, and Zn.), a divalent metal ammonium orthophosphate (Divalent metal is the same as above.), and a divalent metal orthophosphate (Divalent metal is the same as above.), with the atomic ratio of the divalent metal/vanadium of 0.003-0.5, by calcining the mixture at 300°-400° C., and then pretreating said catalyst in an inert gas or a mixed gas containing n butane and molecular oxygen at 350°-700° C. Maleic anhydride can be manufactured at a high conversion, a high selectivity and a high yield according to the present invention.

8 Claims, No Drawings

PROCESS FOR THE MANUFACTURE OF MALEIC ANHYDRIDE

BACKGROUND OF THE INVENTION

1. Field of the Invention:

The present invention relates to a process for the manufacture of maleic anhydride by a vapor phase catalytic oxidation of n-butane with molecular oxygen, and, in particular, to a process for the manufacture of maleic anhydride using a phosphorus vanadium oxygen composite catalyst prepared by a specific process and containing specific metals.

2. Description of the Prior Art:

Processes for the manufacture of maleic anhydride by a vapor phase catalytic oxidation of n-butane using molecular oxygen are conventionally well known in the art. Various types of catalysts used in the processes have been proposed or reported. For example, British Patent No. 1,399,560 proposes a phosphorus vanadium-oxygen composite catalyst containing Cr, Fe, Hf, Zr, La, or Ce; U.S. Pat. No. 3,862,146 discloses a phosphorus vanadium oxygen composite catalyst containing Zn, Cu, Bi, or Li; and U.S. Pat. No. 3,987,063 describes a phosphorus vanadium oxygen composite catalyst containing Co, Ni, or Cd. In addition, "Shokubai", Vol. 33, No. 2, pp 115-118 (1991) presents a report dealing with the catalytic activity of a phosphorus-vanadium oxygen composite catalyst containing Mo, Sb, Cr, Fe, As, Mn, Sn, Co, Cu, Zn, W, Ca, Mg, Na, K, or Cs. These conventional phosphorus vanadium oxygen composite catalysts containing various kinds of metals proposed or reported heretofore, however, are not satisfactory in their catalytic activity, the selectivity for maleic anhydride, and the like. Improvements in their performances are therefore desired.

SUMMARY OF THE INVENTION

An object of the present invention is to provide an efficient process for preparing maleic anhydride by a vapor phase catalytic oxidation of n-butane with molecular oxygen by the utilization of a specific catalyst.

Another object of the Present invention is to provide a catalyst exhibiting a superior catalytic activity and excellent selectivity for maleic anhydride to use in a process for a vapor phase catalytic oxidation of n butane using molecular oxygen.

Other objects of the present invention will be apparent to the person in the art from the following detailed descriptions and embodiments.

I have undertaken extensive studies in order to achieve the above objects. As a result, I have found that the insufficient catalytic activity and selectivity for maleic anhydride are resulted from inadequate process in the preparation of phosphorus-vanadium-oxygen composite catalysts containing various kinds of metals, and that the catalytic activity and selectivity for maleic anhydride can be remarkably improved by the use of a specific process for preparation of catalyst. Specifically, according to a conventional process of the catalyst preparation, a catalyst precursor solution is prepared from a vanadium compound (e.g., vanadium pentoxide), a reducing agent (e.g., hydrogen chloride) and a phosphorus compound (e.g., orthophosphoric acid) by adding a solution containing various metal compounds (e.g., metal chlorides), evaporating the precursor solution to make a solid material, and calcining the solid material.

According to my finding, a catalyst prepared by a process comprising preparing solid vanadyl hydrogen orthophosphate ($VOHPO_4 \cdot 0.5H_2O$) from a vanadium compound, a reducing agent and a phosphorus compound, mixing the vanadyl hydrogen orthophosphate with a divalent metal hydrogen orthophosphate, a divalent metal ammonium orthophosphate, or a divalent metal orthophosphate at a specified ratio, and calcining the mixture, exhibits remarkably improved catalytic activity and selectivity for maleic anhydride. In addition, I have found that specific kinds of divalent metals should be used in the catalyst for achieving the intended object. Furthermore, I have found that in order to fully achieve the intended object, the catalyst thus prepared should be used after a pretreatment in an inert gas or a mixed gas containing n-butane and molecular oxygen under specific conditions before it is submitted to the vapor phase catalytic oxidation reaction. These findings have led to the completion of the present invention.

Accordingly, the present invention provides in a process for manufacturing maleic anhydride by a vapor phase catalytic oxidation of n butane with molecular oxygen, an improvement which comprises using a catalyst prepared from a mixture of vanadyl hydrogen orthophosphate represented by the formula $VOHPO_4 \cdot 0.5H_2O$ (I) and at least one compound selected from the group consisting of a divalent metal hydrogen orthophosphate represented by the formula $MHPO_4 \cdot nH_2O$ (II) wherein M is a divalent metal selected from the group consisting of Mg, Ca, Ba, Mn, Fe, Co, Ni, Cu and Zn and n is a number of coordinated water which differs depending on the temperature at which the compound is prepared, a divalent metal ammonium orthophosphate represented by the formula $NH_4MPO_4 \cdot nH_2O$ (III) wherein M and n have the same meanings as defined above, and a divalent metal orthophosphate represented by the formula $M_3(PO_4)_2 \cdot nH_2O$ (IV) wherein M and n have the same meanings as defined above, with the atomic ratio of M/V (M has the same meaning as defined above, hereinafter the same.) of 0.003-0.5, by calcining the mixture at 300°-400° C., and then pretreating said catalyst in an inert gas or a mixed gas containing n-butane and molecular oxygen at 350°-700° C.

DETAILED DESCRIPTION OF THE INVENTION

In order to achieve the intended object of the present invention, it is essential to adjust the proportion of vanady hydrogen orthophosphate (I) and a divalent metal hydrogen orthophosphate (II), a divalent metal ammonium orthophosphate (III), or a divalent metal orthophosphate (IV) such that the atomic ratio of M/V be in the range of 0.003-0.5. If the atomic ratio of M/V is less than 0.003 or greater than 0.5, the intended effect of the present invention cannot be obtained. A preferable proportion of blend, in terms of the M/V atomic ratio, is in the range of 0.01-0.2. If the M/V atomic ratio is smaller than 0.01, a significant improvement in the selectivity for maleic anhydride cannot be realized, even though there is a considerable improvement in the catalytic activity. On the other hand, if it is greater than 0.2, the improvement in the catalytic activity is not significant, although a considerable improvement in the selectivity for maleic anhydride can be realized.

The divalent metal contained in the divalent metal hydrogen orthophosphate (II), the divalent metal ammonium orthophosphate (III), or the divalent metal orthophosphate (IV) is selected from the group consisting of Mg, Ca, Ba, Mn, Fe, Co, Ni, Cu, and Zn. It is possible to use two or more hydrogen orthophosphates (II), ammonium orthophosphates (III), or orthophosphates (IV) of different divalent metals. Moreover, if desired, it is possible to use two or more compounds selected from hydrogen orthophosphates (II), ammonium orthophosphates (III), and orthophosphates (IV). The vanadyl hydrogen orthophosphate (I), a divalent metal hydrogen orthophosphate (II), a divalent metal ammonium orthophosphate (III), and a divalent metal orthophosphate (IV) used for the preparation of the catalyst of the present invention can be prepared by any processes conventionally known in the art. For example, they can be prepared by the following processes.

Vanadyl hydrogen orthophosphate (I) can be prepared by reducing a vanadium compound, such as vanadium pentoxide, metavanadic acid, or pyrovanadic acid, or the like, with a reducing agent, such as hydrogen chloride, an alcohol, an aldehyde, or the like; reacting the resulting reaction product with a phosphorus compound, such as orthophosphoric acid, pyrophosphoric acid, phosphorus pentoxide, alkali metal phosphate, phosphorus pentachloride, or the like; separating the precipitate from the resulting reaction mixture; thoroughly washing the precipitate; and drying it.

A divalent metal hydrogen orthophosphate (II) can be prepared by adding a solution of a compound, e.g.. a chloride. sulfate, nitrate or organic acid salt of said divalent metal to an aqueous solution of dialkali metal (e.g., sodium, potassium, etc.) hydrogen orthophosphate or alkali metal dihydrogen orthophosphate maintained pH 4–5; separating the precipitate from the resulting reaction mixture; thoroughly washing the precipitate; and drying it. Among the above divalent metals, if the divalent metal is Mg, Ca, or Ba, the desired hydrogen orthophosphate (11) can also be produced by using an aqueous solution of ammonium dihydrogen orthophosphate or diammonium hydrogen orthophosphate.

A divalent metal ammonium orthophosphate (III) can be prepared by adding, in the same manner as above, a compound of a divalent metal, such as illustrated just above, to an excess amount of an aqueous solution of ammonium dihydrogen orthophosphate or diammonium hydrogen orthophosphate; separating the precipitate from the resulting reaction mixture; thoroughly washing the precipitate; and drying it. Among the divalent metals, however, if the divalent metal is Mg, Ca, or Ba, the desired ammonium orthophosphate (III) cannot be obtained by the process just mentioned above, and it is necessary to use a slightly acidic aqueous solution of ammonium dihydrogen orthophosphate or diammonium hydrogen orthophosphate containing an acid such as citric acid or the like.

A divalent metal orthophosphate (IV) can be prepared by adding an aqueous solution of disodium hydrogen orthophosphate or dipotassium hydrogen orthophosphate to an aqueous solution of a divalent metal compound, normally at a molar ratio to give the M/P atomic ratio of about 3/2; separating the Precipitate from the resulting reaction mixture; thoroughly washing the precipitate; and drying it.

The catalyst for use in the process of the present invention can be prepared by preparing a mixture of vanadyl hydrogen orthophosphate (I) and a divalent metal hydrogen orthophosphate (II), a divalent metal ammonium orthophosphate (III), and/or a divalent metal orthophosphate (IV) at a proportion to make the atomic ratio of M/V 0.003–0.5, preferably 0.01–0.2, making the mixture a solution, a suspension or a slurry, as needed, preferably making it a slightly acidic aqueous solution of pH 4–5, heating the mixture, evaporating the mixture to make a solid material, and calcining the solid material at 300°–400° C. The calcination may be carried out either in a gas containing molecular oxygen such as air or in an inert gas such as nitrogen. Incidentally, calcination in an inert gas is preferred when iron hydrogen orthophosphate or iron ammonium orthophosphate is used, because they are unstable in air. An appropriate period of time for which the solid material is calcined is 30 minutes to 12 hours. Before submitting the catalyst thus prepared to a vapor phase catalytic oxidation reaction, it is imperative to pretreat it in an inert gas such as nitrogen, carbon dioxide, or the like or in a mixed gas of n-butane and molecular oxygen, i.e., a raw material for the vapor phase catalytic oxidation, at 350°–700° C. The pretreatment temperature is important for the catalyst to exhibit desired catalytic activity. If the temperature is lower than 350° C., desired catalytic activity cannot be obtained whereas if higher than 700° C., the catalytic activity is lost. The pretreatment is suitably carried out for a period of 30 minutes to 20 hours.

The vapor phase catalytic oxidation reaction for the manufacture of maleic anhydride in the present invention may be carried out under the conditions generally known in the art. Normally, the reaction is carried out as follows. As a raw material gas, a mixed gas comprising 1–4 vol.% of n-butane, 10–20 vol.% of molecular oxygen, and 76–89 vol.% of a diluent gas is introduced over the pretreated catalyst described above at a temperature of 300°–500° C. under any optional pressure, normally under the atmospheric pressure. at a gas hourly space velocity of 300–5000/hr$^{-1}$ calculated under normal pressure. Air is normally used as the molecular oxygen, although pure oxygen may be used. It is needless to mention that when air is used, the addition of a diluent gas is not required depending on the desired molecular oxygen concentration. An inert gas such as nitrogen, carbon dioxide, or the like is normally used as the diluent gas in industrial applications.

According to the present invention, maleic anhydride can be obtained economically in a high yield and in a high selectivity, since the catalyst has a high catalytic activity and superior selectivity for maleic anhydride in the manufacture of maleic anhydride by the vapor phase catalytic oxidation of n-butane with molecular oxygen.

DESCRIPTION OF THE PREFERRED EMBODIMENTS

The present invention is hereinafter described in more detail by way of examples, but they are given only for illustration and the present invention is not limited thereby. Conversion, selectivity, and yield have the meanings as defined below:

Conversion: [Moles of n-butane reacted / Moles of n butane charged] × 100

Selectivity: [Moles of maleic anhydride produced / Moles of n butane reacted] × 100

Yield: [Moles of maleic anhydride produced / Moles of n butane charged] × 100

Example 1

10 g of vanadium pentoxide was added to 80 ml of benzyl alcohol and the mixture was heated while stirring. After confirming that vanadium pentoxide was reduced, 11.3 g of 98% orthophosphoric acid was added thereto, and followed by refluxing for 1 hour. The precipitate produced was separated and washed thoroughly with toluene, and dried at 120° C. to obtain vanadyl hydrogen orthophosphate [$VOHPO_4 \cdot 0.5H_2O$] (I).

An aqueous solution obtained by dissolving 13.2 g of magnesium acetate in 100 ml of water and an aqueous solution obtained by dissolving 11.5 g of ammonium dihydrogen orthophosphate in 100 ml of water were slowly mixed together, in portions, the same amount of each solution at a time, while maintaining the pH at 4.

The mixture was allowed to stand overnight and the precipitate produced was separated. The precipitate was washed thoroughly with water, and dried at 80° C. to obtain magnesium hydrogen orthophosphate [$MgHPO_4 \cdot 3H_2O$] (II).

The vanadyl hydrogen orthophosphate (I) and the magnesium hydrogen orthophosphate (II) were mixed at a proportion such that the atomic ratio of Mg/V be 0.05. The mixture was added to an aqueous solution with pH 4 obtained by adding hydrochloric acid to distilled water, and heated at 80°–100° C. for 4 hours while stirring. The solution thus obtained was evaporated at 120° C. to obtain a solid material. The solid material was calcined at 360° C. in air for 6 hours and pelletized to make the catalyst.

3 g of the pelletized catalyst was filled into a fixed bed flow type reactor and pretreated by passing through a raw material gas consisting of 2 vol.% of n-butane, 20 vol.% of oxygen, and 78 vol.% of helium under the conditions of a temperature of 460° C. and a gas hourly space velocity of $1800/hr^{-1}$ under atmospheric pressure for 6 hours. The performances of the catalyst were then evaluated under the same conditions as employed for the pretreatment, except that the reaction temperature of 440° C. was used. The results are shown in Table 1.

Example 2

Vanadyl hydrogen orthophosphate (I) was prepared in the same manner as in Example 1.

An aqueous solution obtained by dissolving 11 g of calcium dichloride in 100 ml of water and an aqueous solution obtained by dissolving 11.5 g of ammonium dihydrogen orthophosphate in 100 ml of water were mixed by gradually adding equal amounts of both of the aqueous solutions keeping pH at 4. The mixture was kept to stand for 24 hours, and then, a precipitate thus formed was recovered. The precipitate was washed well with water, and dried at 80° C., thereby obtained calcium hydrogen orthophosphate [$CaHPO_4 \cdot 2H_2O$] (II).

The vanadyl hydrogen orthophosphate (I) and the calcium hydrogen orthophosphate (II) obtained above were mixed together in a ratio to give Ca/v atomic ratio of 0.10 and distilled water was added thereto. The mixture was stirred for 4 hours at a temperature range of 80°–100° C. with heating, and the slurry thus obtained was evaporated at 120° C. to give a solid material. The solid material was calcined in air in the same manner as in Example 1. The calcined material was pelletized thereby obtained a catalyst.

The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment, except that the reaction temperature of 430° C. was used. The results are shown in Table 1.

Example 3

Vanadyl hydrogen orthophosphate (I) was prepared in the same manner as in Example 1. An aqueous solution obtained by dissolving 12.6 g of manganese dichloride in 100 ml of water was added to an aqueous solution obtained by dissolving 20 g of disodium hydrogen orthophosphate in 100 ml of water, and a precipitate thus formed was recovered. The precipitate thus formed was washed well with water, and dried at 80° C., thereby obtained manganese hydrogen orthophosphate [$MnHPO_4 \cdot 3H_2O$](II). The vanadyl hydrogen orthophosphate (I) and the manganese hydrogen orthophosphate (11) obtained above were mixed in a ratio to give Mn/V atomic ratio of 0.03 and the mixture was added to an aqueous solution of orthophosphoric acid with pH 4 and stirred for 4 hours at a temperature range of 80°–100° C. with heating. Then, resultant solution was evaporated to give a solid material. The solid material was calcined in air in the same manner as in Example 1. A catalyst was prepared by pelletizing the calcined material. The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment, except that the reaction temperature of 410° C. was used. The results are shown in Table 1.

Example 4

Vanadyl hydrogen orthophosphate (I) was prepared in the same manner as in Example 1. An aqueous solution obtained by dissolving 0.4 g of iron dichloride in 10 ml of water was added to an aqueous solution obtained by dissolving 6 g of ammonium dihydrogen orthophosphate in 100 ml of water under a nitrogen atmosphere so as to avoid a contact with oxygen, and a precipitate thus formed was recovered. After washing the precipitate with ethanol several times, the precipitate was dried at 80° C., thereby obtained iron ammonium orthophosphate [$NH_4FePO_4 \cdot 6H_2O$] (III).

Into 100 ml of ethanol, the vanadyl hydrogen orthophosphate (I) and the iron ammonium orthophosphate (III) were added simultaneously and then, ethanol was evaporated by stirring the mixture under a nitrogen atmosphere at 50° C., thereby obtained a solid material. The solid material was calcined in the same manner as in Example 1 except that the calcination was conducted in a nitrogen atmosphere. A catalyst was prepared by pelletizing the calcined material. The Fe/V atomic ratio of the catalyst thus prepared was 0.03. The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment except that the reaction temperature of 400° C. was used. The results are shown in Table 1.

Example 5

Vanadyl hydrogen orthophosphate (I) was prepared in the same manner as in Example 1.

An aqueous solution obtained by dissolving 13.1 g of cobalt dichloride in 100 ml of water was added to an aqueous solution obtained by dissolving 20 g of ammonium dihydrogen orthophosphate in 100 ml of water, and stirred for 7 hours at 60° C., and a precipitate thus formed was recovered. The precipitate was washed well with water, and dried at 60° C., thereby obtained cobalt ammonium orthophosphate [$NH_4CoPO_4 \cdot 6H_2O$] (III). The Vanadyl hydrogen orthophosphate (I) and the cobalt ammonium orthophosphate (III) obtained above were mixed in a ratio to give Co/V atomic ratio of 0.03 and a solid material was obtained in the same manner as in Example 1. The solid material was calcined in air in the same manner as in Example 1 and was pelletized to form a catalyst. The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment except that the reaction temperature of 400% was used. The results are shown in Table 1.

Example 6

Vanadyl hydrogen orthophosphate (I) was prepared in the same manner as in Example 1.

An aqueous solution obtained by dissolving 13.6 g of zinc dichloride in 100 ml of water was added to an aqueous solution obtained by dissolving 20 g of ammonium dihydrogen orthophosphate in 100 ml of water, and zinc hydrogen orthophosphate [$NH_4ZnPO_4 \cdot 6H_2O$] (III) was obtained by the same procedure as in Example 5.

The Vanadyl hydrogen orthophosphate (I) and the zinc ammonium orthophosphate (III) obtained above were mixed in a ratio to give Zn/V atomic ratio of 0.10 and a solid material was obtained by the same procedure as in Example 3. The solid material was calcined in air in the same manner as in Example 1 and was pelletized to form a catalyst. The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment except that the reaction temperature of 420° C. was used. The results are shown in Table 1.

Example 7

Vanadyl hydrogen orthophosphate (1) was prepared in the same manner as in Example 1.

An aqueous solution obtained by dissolving 24.4 g of barium dichloride. dihydrate in 100 ml of water and an aqueous solution obtained by dissolving 12 g of ammonium dihydrogen orthophosphate in 100 ml of water were mixed and barium hydrogen orthophosphate [$BaHPO_4 \cdot 2H_2O$] (II) was obtained by the procedure similar to Example 2.

The Vanadyl hydrogen orthophosphate (I) and the barium hydrogen orthophosphate (II) obtained above were mixed in a ratio to give Ba/V atomic ratio of 0.10 and a solid material was obtained in the same procedure as in Example 2. The solid material was calcined in air in the same manner as in Example 1 and the calcined material was pelletized to form a catalyst. The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment except that the reaction temperature of 440° C. was used. The results are shown in Table 1.

Example 8

Vanadyl hydrogen orthophosphate (I) was prepared in the same manner as in Example 1.

An aqueous solution obtained by dissolving 23.8 g of nickel dichloride hexahydrate in 100 ml of water was added to an aqueous solution obtained by dissolving 20 g of ammonium dihydrogen orthophosphate in 100 ml of water, and nickel ammonium orthophosphate [$NH_4NiPO_4 \cdot 6H_2O$] (III) was Prepared in the same manner as in Example 5.

The Vanadyl hydrogen orthophosphate (I) and the nickel ammonium orthophosphate (III) obtained above were mixed in a ratio to give Ni/V atomic ratio of 0.10, and a solid material was obtained in the same procedure as in Example 2. The solid material was calcined in air in the same manner as in Example 1 and the calcined material was pelletized to form a catalyst. The performances of the catalyst were evaluated by using 3 g of the pelletized catalyst. Prior to use, the catalyst was pretreated under the same conditions as in Example 1, and then, the performances of the catalyst were evaluated under the same conditions as in the pretreatment except that the reaction temperature of 420° C. was used. The results are shown in Table 1.

Example 9

Vanadyl hydrogen orthophosphate (I) was prepared in the same manner as in Example 1.

An aqueous solution obtained by dissolving 17.1 g of copper dichloride dihydrate in 100 ml of water was added to an aqueous solution obtained by dissolving 20 g of ammonium dihydrogen orthophosphate in 100 ml of water, and copper ammonium orthophosphate [$NH_4CuPO_4 \cdot 2H_2O$] (III) was prepared in the same manner as in Example 5.

The Vanadyl hydrogen orthophosphate (I) and the copper ammonium orthophosphate (III) obtained above were mixed in a ratio to give Ni/V atomic ratio of 0.10, and a solid material was obtained in the same procedure as in Example 2. The solid material was calcined in air in the same manner as in Example 1 and the calcined material was pelletized to form a catalyst. The performances of the catalyst were evaluated by using 3 g of the pelletized catalyst. Prior to use, the catalyst was subjected to a pretreatment step under the same conditions as in Example 1, and then, the performances of the catalyst were evaluated under the same conditions as in the pretreatment step except that the reaction temperature of 420° C. was used. The results are shown in Table 1.

Example 10

Vanadyl hydrogen orthophosphate (I) was prepared in the same manner as in Example 1 except that 12.0 g of orthophosphoric acid (purity: 98%) was used.

An aqueous solution obtained by dissolving 9.5 g of magnesium dichloride in 100 ml of water and an aqueous solution obtained by dissolving 9.5 g of disodium hydrogen orthophosphate in 100 ml of water were mixed by gradually adding equal amounts of both of the solutions, and the mixture was kept to stand over a day and night, i.e., 24 hours., and then, a precipitate thus formed was recovered. The precipitate was washed well with water and dried at 80° C. Thus, magnesium orthophosphate [$Mg_3(PO_r)_2 \cdot 8H_2O$] (IV) was obtained.

10 g of the vanadyl hydrogen orthophosphate (1) and 1 g of the magnesium orthophosphate (IV) obtained above (Mg/V atomic ratio was 0.13.) were mixed well in 50 ml of distilled water, and the mixture was dried at 100° C. Thus, a solid material was obtained. The solid material was calcined in air in the same manner as in Example 1 and the calcined material was pelletized to form a catalyst. The performances of the catalyst were evaluated by using 3 g of the pelletized catalyst. Prior to use, the catalyst was subjected to a pretreatment step under the same conditions as in Example 1 except that the gas hourly space velocity was changed to 2400 $hr^{-1}$. Then, the performances of the catalyst were evaluated under the same conditions as n the pretreatment step except that the reaction temperature of 400° C. was used. The results are shown in Table 1.

Example 11

Vanadyl hydrogen orthophosphate (I) was prepared in the same manner as in Example 10.

An aqueous solution obtained by dissolving 12.6 g of manganese dichloride in 100 ml of water and an aqueous solution obtained by dissolving 9.5 g of disodium hydrogen orthophosphate in 100 ml of water were mixed by gradually adding equal amounts of both of the solutions. The mixture was kept to stand for 24 hours, and then, a precipitate thus formed was recovered. The precipitate was washed well with water and dried at 80° c. Thus manganese orthophosphate [$Mn_3 (PO_r)_2 \cdot 5H_2O$] (IV) was obtained.

10 g of the vanadyl hydrogen orthophosphate (I) and 1 g of the manganese orthophosphate (IV) obtained above (Mn/V atomic ratio was 0.12.) were mixed well in 50 ml of distilled water, and the mixture was dried at 100° C. Thus, a solid material was obtained. The solid material was calcined in air in the same manner as in Example 1 and the calcined material was pelletized to form a catalyst. The performances of the catalyst were evaluated by using 3 g of the pelletized catalyst. Prior to use, the catalyst was subjected to a pretreatment step under the same conditions as in Example 10, and then, the performance of the catalyst were evaluated under the same conditions as in he pretreatment step except that the reaction temperature of 400° C. was used. The results are shown in Table 1.

Example 12

Vanadyl hydrogen orthophosphate (I) was prepared in the same manner as in Example 10.

By using an aqueous solution obtained by dissolving 12.7 g of iron dichloride in 100 ml of water and an aqueous solution obtained by dissolving 9.5 g of disodium hydrogen orthophosphate in 100 ml of water, iron orthophosphate [$Fe_3(PO_4)_2 \cdot 8H_2O$] (IV) was prepared by a procedure similar to that described in Example 11.

10 g of the Vanadyl hydrogen orthophosphate (I) and 1 g of the iron orthophosphate (IV) obtained above (Fe/V atomic ratio was 0.10.) were mixed well in 50 ml of distilled water, the mixture was dried at 100° C. Thus, a solid material was obtained. The solid material was calcined in air in the same manner as in Example 1 and the calcined material was Pelletized to form a catalyst. The performances of the catalyst were evaluated by using 3 g of the pelletized catalyst. Prior to use, the catalyst was subjected to a pretreatment step under the same conditions as in Example 10, and then, the performances of the catalyst were evaluated under the same conditions as in the pretreatment step except that the reaction temperature of 380° C. was used. The results are shown in Table 1.

Example 13

Vanadyl hydrogen orthophosphate (I) was prepared in the same manner as in Example 10.

By using an aqueous solution obtained by dissolving 13.0 g of cobalt dichloride in 100 ml of water and an aqueous solution obtained by dissolving 9.5 g of disodium hydrogen orthophosphate in 100 ml of water, cobalt orthophosphate [$CO_3(PO_4)_2 \cdot 8H_2O$] (IV) was prepared by a procedure similar to that described in Example 11.

10 g of the vanadyl hydrogen orthophosphate (I) and 1 g of the cobalt orthophosphate (IV) obtained above (Co/V atomic ratio was 0.10.) were mixed well in 50 ml of distilled water, and the mixture was dried at 100° C. Thus, a solid material was obtained. The solid material was calcined in the same manner as in Example 1 except that a nitrogen gas atmosphere was employed. The calcined material was pelletized to form a catalyst. The performances of the catalyst were evaluated by using 3 g of the pelletized catalyst. Prior to use, the catalyst was subjected to a pretreatment step under the same conditions as in Example 10, and then, the performances of the catalyst were evaluated under the same conditions as in the pretreatment step except that the reaction temperature of 380° C. was used. The results are shown in Table 1.

Example 14

Vanadyl hydrogen orthophosphate (I) was prepared in the same manner as in Example 10.

By using an aqueous solution obtained by dissolving 13.0 g of nickel dichloride in 100 ml of water and an aqueous solution obtained by dissolving 9.5 g of disodium hydrogen orthophosphate in 100 ml of water, nickel orthophosphate [$Ni_3(PO_4)_2 \cdot 8H_2O$] (IV) was prepared by a procedure similar to that described in Example 11.

10 g of the vanadyl hydrogen orthophosphate (I) and 1 g of the nickel orthophosphate (IV) obtained above (Ni/V atomic ratio was 0.10.) were mixed well in 50 ml of distilled water, and the mixture was dried at 100° C. Thus, a solid material was obtained. The solid material was calcined in air in the same manner as in Example 1, and the calcined material was pelletized to form a catalyst. The performances of the catalyst were evaluated by using 3 g of the pelletized catalyst. Prior to use, the catalyst was subjected to a pretreatment step under the same conditions as in Example 10, and then, the performances of the catalyst were evaluated under the same conditions as in the pretreatment step except that the reaction temperature of 400° C. was used. The results are shown in Table 1.

Example 15

Vanadyl hydrogen orthophosphate (I) was prepared in the same manner as in Example 10.

By using an aqueous solution obtained by dissolving 13.4 g of copper dichloride in 100 ml of water and an aqueous solution obtained by dissolving 9.5 g of disodium hydrogen orthophosphate in 100 ml of water, copper orthophosphate [$Cu_3(PO_4)_2 \cdot 3H_2O$] (IV) was prepared by a procedure similar to that described in Example 11.

10 g of the vanadyl hydrogen orthophosphate (I) and 1 g of the copper orthophosphate (IV) obtained above (Cu/V atomic ratio was 0.12.) were mixed well in 50 ml of distilled water, and the mixture was dried at 100° C. Thus, a solid material was obtained. The solid material was calcined in air in the same manner as in Example 1, and the calcined material was pelletized to form a catalyst. The performances of the catalyst were evaluated by using 3 g of the pelletized catalyst. Prior to use, the catalyst was subjected to a pretreatment step under the same conditions as in Example 10, and then, the performances of the catalyst were evaluated under the same conditions as in the pretreatment step except that the reaction temperature of 400° C. was used. The results are shown in Table 1.

Example 16

Vanadyl hydrogen orthophosphate (I) was prepared in the same manner as in Example 10.

By using an aqueous solution obtained by dissolving 13.6 g of zinc dichloride in 100 ml of water and an aqueous solution obtained by dissolving 9.5 g of disodium hydrogen orthophosphate in 100 ml of water, zinc orthophosphate [$Zn_3(PO_4)_2 \cdot 4H_2O$] (IV) was prepared by a procedure similar to that described in Example 11.

10 g of the vanadyl hydrogen orthophosphate (I) and 1 g of the zinc orthophosphate (IV) obtained above (Zn/V atomic ratio was 0.12.) were mixed well in 50 ml of distilled water, and the mixture was dried at 100° C. Thus, a solid material was obtained. The solid material was calcined in air as in Example 1, and the calcined material was pelletized to form a catalyst. The performances of the catalyst were evaluated by using 3 g of the pelletized catalyst. Prior to use, the catalyst was subjected to a pretreatment step under the same conditions as in Example 10, and then, the performances of the catalyst were evaluated under the same conditions as in the pretreatment step except that the reaction temperature of 380° C. was used. The results are shown in Table 1.

Example 17

This example is given for comparative purpose, and is not within the scope of this invention.

10 g of vanadium pentoxide was added to 80 ml of benzyl alcohol, and the mixture was stirred with heating.

After it was confirmed that vanadium pentoxide had been reduced, 12.4 g of orthophosphoric acid having purity of 98% was added thereto, and refluxed for 1 hour. Then, a precipitate thus formed was recovered. The precipitate was washed well with toluene and then dried at 120° C. Thus, vanadyl hydrogen orthophosphate [$VOHPO_4 \cdot 0.5H_2O$] (I) was obtained. The vanadyl hydrogen orthophosphate (I) was calcined in air at 360° C. for 6 hours to produce a catalyst. The catalyst was vanadyl pyrophosphate [$(VO)_2P_2O_7$] containing a small amount of additional phosphorus compounds and had P/V atomic ratio of 1.1.

The catalyst was pelletized before use. The performances of the catalyst were evaluated by using 3 g of the pelletized catalyst. Prior to use, the catalyst was subjected to a pretreatment step under the same conditions as in Example 1, and then, the performances of the catalyst were evaluated under the same conditions as in the pretreatment step except that in one run, the reaction temperature of 440° C. was used, and in another run, the reaction temperature of 470° C. was used. The results are shown in Table 1.

Example 18

This example is given for comparative purpose, and is not within the scope of this invention.

Vanadyl pyrophosphate [$(VO)_2P_2O_7$] was prepared in the same manner as in Example 17. A catalyst was prepared by pelletizing the vanadyl pyrophosphate obtained above. The performances of the catalyst were evaluated by using 3 g of the pelletized catalyst. Prior to use, the catalyst was subjected to a Pretreatment step under the same conditions as in Example 10, and then, the performances of the catalyst were evaluated under the same conditions as in the pretreatment step except that in one run, the reaction temperature of 400° C. was used, and in another run, the reaction temperature of 70° C. was used. The results are shown in Table 1.

Example 19

This example is given for comparative purpose, and is not within the scope of this invention.

Magnesium hydrogen orthophosphate [$MgHPO_4 \cdot 3H_2O$] (II) which was the same material as that obtained in Example 1, was calcined in air at 360° C. for 6 hours, and then at 460° C. for 6 hours. Thus, a catalyst was obtained. The catalyst thus prepared was magnesium pyrophosphate [$Mg_2P_2O_7$]. The catalyst was pelletized. The performances of the catalyst were evaluated by using 3 g of the pelletized catalyst. Prior to use, the catalyst was subjected to a pretreatment step under the same conditions as in Example 1, and then, the performances of the catalyst were evaluated under the same conditions as in the pretreatment step except that the reaction temperature of 440° C. was used. The results are shown in Table 1.

Example 20

This example is given for comparative purpose, and is not within the scope of this invention.

Cobalt orthophosphate [$CO_3(PO_4)_2 \cdot 8H_2O$] (IV) which was the same material as that obtained in Example 13, was calcined in air at 360° C. for 6 hours, and then at 460° C. for 6 hours. Thus, a catalyst was obtained. The catalyst thus prepared was cobalt orthophosphate [$CO_3(PO_4)_2$]. The catalyst was pelletized. The performances of the catalyst were evaluated by using 3 g of the pelletized catalyst. Prior to use, the catalyst was subjected to a pretreatment step under the same conditions as in Example 10, and then, the performances of the catalyst were evaluated under the same conditions as in the pretreatment step except that the reaction temperature of 400° C. was used. The results are shown in Table 1.

Example 21

This example is given for comparative purpose, and is not within the scope of this invention.

Into 100 ml of water, 11 g of orthophosphoric acid (purity: 98%) and 7 g of hydrochloric acid salt of hydroxylamine were added. Then, 9.1 g of vanadium pentoxide was gradually added thereto with stirring at 80° C. with heating. The vanadium pentoxide added was dissolved thereby. Into a dark blue solution thus obtained, 10 ml of an aqueous solution containing 1.3 g of manganese dichloride was added with stirring. Then, the mixture was concentrated by evaporation, and was dried to obtain a solid material. The solid material was calcined in a nitrogen gas stream at 500° C. for 2 hours. Thus, a catalyst having Mn/V atomic ratio of 0.10 was obtained. The catalyst was pelletized. The performances of the catalyst were evaluated by using 3 g of the pelletized catalyst. Prior to use, the catalyst was subjected to a pretreatment step under the same conditions as in Example 1, and then, the performances of the catalyst were evaluated under the same conditions as in the pretreatment step except that the reaction temperature of 430° C. was used. The results are shown in Table 1.

Example 22

This example is given for comparative purpose, and is not within the scope of this invention.

A catalyst having Mn/V atomic ratio of 0.10 was prepared in the same manner as in Example 21. The performances of the catalyst were evaluated by using 3 g of the pelletized catalyst. Prior to use, he catalyst was subjected to a pretreatment step under the same conditions as in Example 10, and then, the performances of the catalyst were evaluated under the same conditions as in the pretreatment step except that in one run, the reaction temperature of 400° C. was used, and in another run, the reaction temperature of 440° C. was used. The results are shown in Table 1.

TABLE 1

| Example No. | Temperature (°C.) | Catalyst Performances | | |
|---|---|---|---|---|
| | | Conversion (%) | Selectivity (%) | Yield (%) |
| 1 | 440 | 85 | 74 | 62.9 |
| 2 | 430 | 86 | 70 | 60.2 |
| 3 | 410 | 90 | 72 | 64.8 |
| 4 | 400 | 95 | 76 | 72.2 |
| 5 | 400 | 84 | 74 | 62.2 |
| 6 | 420 | 84 | 76 | 63.8 |
| 7 | 440 | 84 | 71 | 59.6 |
| 8 | 420 | 88 | 66 | 58.1 |
| 9 | 420 | 82 | 68 | 55.8 |
| 10 | 400 | 86 | 72 | 61.9 |
| 11 | 400 | 90 | 69 | 62.1 |
| 12 | 380 | 92 | 71 | 65.3 |
| 13 | 380 | 89 | 73 | 65.0 |
| 14 | 400 | 84 | 76 | 63.8 |
| 15 | 400 | 94 | 67 | 62.9 |
| 16 | 380 | 93 | 70 | 65.1 |
| 17 | 440 | 52 | 66 | 34.3 |
| | 470 | 86 | 62 | 53.3 |
| 18 | 400 | 16 | 79 | 12.6 |
| | 470 | 87 | 61 | 53.1 |
| 19 | 440 | 10 | 4 | 0.4 |
| 20 | 400 | 4 | 20 | 0.8 |
| 21 | 430 | 90 | 60 | 54.0 |
| 22 | 400 | 36 | 76 | 27.4 |
| | 440 | 84 | 64 | 53.8 |

Obviously, numerous modifications and variations of the present invention are possible in light of the above teachings. It is therefore to be understood that within the scope of the appended claims, the invention may be practiced otherwise than as specifically described herein.

I claim:

1. In a process for manufacturing maleic anhydride by the vapor phase catalytic oxidation of n-butane with molecular oxygen, an improvement which comprises using a catalyst prepared by mixing vanadyl hydrogen orthophosphate represented by the formula $VOHPO_4 \cdot 0.5H_2O$ (I), and at least one compound selected from the group consisting of a divalent metal hydrogen orthophosphate represented by the formula $MHPO_4 \cdot nH_2O$ (II) wherein M is a divalent metal selected from the group consisting of Mg, Ca, Ba, Mn, Fe, Co, Ni, Cu and Zn and n is a number of coordinated water which differs depending on the temperature at which the compound is prepared, a divalent metal ammonium orthophosphate represented by the formula $NH_4MPO_4 \cdot nH_2O$ (III) wherein M and n have the same meanings as defined above and a divalent metal orthophosphate represented by the formula $M_3(PO_4)_2 \cdot nH_2O$ (IV) wherein M and n have the same meanings as defined above, with the atomic ratio of M/V (M has the same meaning as defined above) of 0.003–0.5, by calcining the mixture at 300°–400° C., and then pretreating said catalyst in an inert gas or a mixed gas containing n butane and molecular oxygen at 350°–700° C.

2. A process according to claim 1, wherein said vanadyl hydrogen orthophosphate (I) and at least one species selected from the group consisting of said divalent metal hydrogen orthophosphate (II), said divalent metal ammonium orthophosphate (III) and said divalent metal orthophosphate (IV) are mixed as a solution, a suspension or a slurry.

3. A process according to claim 1, wherein said vanadyl hydrogen orthophosphate (I) and at least one species selected from the group consisting of said divalent metal hydrogen orthophosphate (II), said divalent metal ammonium orthophosphate (III) and said divalent metal orthophosphate (IV) are mixed as an aqueous solution having a very week acidity within a range of pH 4–5.

4. A process according to claim 1, wherein said calcination of said mixture of said vanadyl hydrogen orthophosphate (I) and at least one species selected from the group consisting of said divalent metal hydrogen orthophosphate (II), said divalent metal ammonium orthophosphate (III) and said divalent metal orthophosphate (IV) is conducted for a period of time within a range of from 30 minutes to 12 hours.

5. A process according to claim 1, wherein the time for the pretreatment of the prepared catalyst is within a range of from 30 minutes to 20 hours.

6. A process according to claim 1, wherein the gas for the pretreatment of the prepared catalyst is a mixed gas containing n butane and molecular oxygen and having the same composition as that of the raw material gas for said vapor phase catalytic oxidation.

7. A process according to claim 1, wherein the raw material gas for said vapor phase catalytic oxidation contains 1–4 vol.% of n butane, 10–20 vol.% of molecular oxygen and 76–89 vol.% of an inert gas.

8. A process according to claim 1, wherein the temperature of said vapor phase catalytic oxidation is within a range from 300°–500° C.

* * * * *